United States Patent [19]

Goto et al.

[11] Patent Number: 5,496,715
[45] Date of Patent: Mar. 5, 1996

[54] PROCESS FOR PREPARING INDIGO

[75] Inventors: Makoto Goto, Ami; Terukazu Nara, Ibaraki; Masato Terasawa; Hideaki Yukawa, both of Ami, all of Japan

[73] Assignees: Mitsubishi Chemical Corporation; Petroleum Energy Center, both of Tokyo, Japan

[21] Appl. No.: 293,969

[22] Filed: Aug. 24, 1994

[30] Foreign Application Priority Data

Aug. 25, 1993 [JP] Japan .................................. 5-210439
Apr. 14, 1994 [JP] Japan .................................. 6-075678

[51] Int. Cl.$^6$ ........................... C12P 1/04; C12P 17/16; C12P 17/18
[52] U.S. Cl. ..................... 435/170; 435/118; 435/119; 435/121; 435/822
[58] Field of Search ................... 435/170, 822, 435/119, 118, 121

[56] References Cited

FOREIGN PATENT DOCUMENTS 4-287691  10/1992  Japan .

OTHER PUBLICATIONS

Nature, vol. 196, Nov. 24, 1962, pp. 793–795, O. K. Sebek, et al., "Divergent Pathways of Indole Metabolism in Chromobacterium Violaceum".

Biochimica et Biophysica Acta, vol. 158, 1968, pp. 70–78, M. Fujioka, et al., "The Bacterial Oxidation of Indole".

Science, vol. 222, Oct. 14, 1983, pp. 167–169, B. Ensley, et al., "Expression of Naphthalene Oxidation Genes in *Escherichia Coli* Results in the Biosynthesis of Indigo".

Applied Biochemistry and Biotechnology, vol. 30, 1991, pp. 303–312, J. Eyal, et al., "Production of Indigotin in Submerged Culture Using Morchella Nov. ES-1".

Journal of General Microbiology, vol. 138, 1992, pp. 205–209, S. Hart, et al., "Construction of an Insertional–Inactivation Cloning Vector for *Escherichia Coli* Using a Rhodococcus Gene for Indigo Production".

*Primary Examiner*—Herbert J. Lilling
*Attorney, Agent, or Firm*—Oblon, Spivak, McClelland, Maier & Neustadt

[57] ABSTRACT

There is disclosed a process for preparing indigo which comprises bringing an indigo-producing bacteria belonging to genus Acinetobacter or treated products thereof into contact with an aqueous solution containing at least indole to have indigo formed and accumulated in the aqueous solution; and collecting indigo from the aqueous solution.

14 Claims, No Drawings

PROCESS FOR PREPARING INDIGO

BACKGROUND OF THE INVENTION

The present invention relates to a process for preparing indigo from indole efficiently.

Indigo has conventionally been prepared by a chemical synthetic method and has been broadly utilized as a dye for industrial uses. However, the chemical synthetic method is poor in a yield because it requires multiple steps of reactions. It has also a disadvantage that much amounts of byproducts are produced due to the chemical decomposition.

As a promising process among various processes for preparing indigo, there may be mentioned a process for preparing indigo from indole by using a microorganism of genus Pseudomonas (P. M. M. Gray: Proc. Royal Soc. London, Ser. B, Vol. 102, Pages 2263 to 2279 (1928), and Japanese Provisional Patent Publication No. 287691/1992), a process for preparing indigo from indole by using a microorganism of genus Mycobacterium (O. Sebck and H. Aeger: Nature, Vol. 196, Pages 793 to 795 (1962)), a process for preparing indigo from indole by using a microorganism of genus Micrococcus (M. Fujioka and H. Wada: Biochimica et Biophysica Acta, Vol. 158, Pages 70 to 78 (1968)), a process for preparing indigo from indole by using, as an enzymatic catalyst, *Escherichia coli* transformed with a plasmid containing a gene which encodes xyleneoxygenase or naphthaleneoxygenase isolated from a microorganism of genus Pseudomonas (Burt D. Ensley, Barry J. Ratzkin, Timthyl D. Osslund and Mary J. Simon: Science, Vol. 222, Pages 167 to 169 (1983)), a process for preparing indigo from indole by using a microorganism of Morcella species (J. Eyal, Md. A. Mabud, and J. F. Walter: Applied Biochemistry and Biotechnology, Vol. 30, Pages 303 to 312 (1991)), and a process for preparing indigo from indole by using, as an enzymatic catalyst, *Escherichia coli* transformed with a plasmid containing a gene obtained from a microorganism of genus Rhodococcus (S. Hart and D. R. Woods: Journal of General Microbiology, Vol. 138, Pages 205 to 509 (1992)), but a practical technique for preparing indigo has not yet been established and development of a process for efficiently preparing indigo has been desired.

SUMMARY OF THE INVENTION

It is an object of the present invention to prepare indigo in a high yield.

The present inventors have intensively studied in order to establish a process for efficiently preparing indigo and found that strains of genus Acinetobacter efficiently produces indigo to accomplish the present invention.

The present invention is to provide a process for preparing indigo which comprises bringing an indigo-producing bacteria belonging to genus Acinetobacter or treated products thereof into contact with an aqueous solution containing at least indole to have indigo formed and accumulated in the aqueous solution, and collecting indigo from the aqueous solution.

DESCRIPTION OF THE PREFERRED EMBODIMENT

In the following, the present invention is explained in detail.

In the present invention, a strain which belongs to genus Acinetobacter and which has an indigo-producing ability or a mutant strain thereof may be used.

The indigo-producing bacteria to be used in the present invention can be obtained by the method as shown below. For example, a sample of water in a river, grasses, trees or soils is suspended in sterilized water. Then, a portion of the water suspended with these samples are inoculated into the medium containing xylene or benzoic acid as a main carbon source, and the medium is subjected to shaking culture at a temperature of about 30° C. for 48 hours. After that, a portion of the culture broth is inoculated into the same medium and is subjected to shaking culture medium described above. This procedure is repeated several times for enrichment culture of microorganisms which are able to grow on the medium. Then, the culture broth obtained above is spread on a solid medium containing xylene or benzoic acid as a main carbon source. The solid medium is incubated at about 30° C. for one day and single colony obtained on this medium is isolated. Indigo-producing bacteria can be obtained from these isolated colonies or known available strains by the isolation of the strains which produces blue pigments in an indole-containing aqueous solution. To select the strain which belongs to genes Acinetobacter, the bacteriological and taxonomic properties of thus selected indigo-producing strain is examined. And the strains belonging to genus Acinetobacter can be used in the present invention.

As a concrete example thereof, there may be mentioned Acinetobacter species MY-15 strain (hereinafter sometimes abbreviated as "MY-15"), *Acinetobacter calcoaceticus* ATCC 19606 strain (hereinafter sometimes abbreviated as "ATCC 19606"), Acinetobacter species VA-66 strain (hereinafter sometimes abbreviated as "VA-66") and Acinetobacter species VA-251 strain (hereinafter sometimes abbreviated as "VA-251"). MY-15, VA-66 and VA-251 are strains which were newly isolated from soil by the present inventors and have common bacteriological and taxonomic properties as follows:

I. Microscopical properties:
  (a) Morphology and size of cell: rod, 1×2 µm;
  (b) Polymorphism: none;
  (c) Motility: none;
  (d) Spore: none; and
  (e) Gram stain: negative.

II. Cultural properties
  (a) Bouillon agar culture: growth; and
  (b) Utilizable carbon source: fumaric acid, citric acid, malic acid, n-capric acid, adipic acid, ethanol, acetic acid and benzoic acid.

III. Growth condition
  (a) growth temperature: moderate temperature;
  (b) growth pH: neutral; and
  (c) oxygen: required.

IV. Physiological properties
  (a) oxidase: negative;
  (b) catalase: positive;
  (c) gelatin liquefaction: negative;
  (d) reduction of nitrate: negative;
  (e) glucose fermentation: negative; and
  (f) decomposition of urea: negative.

MY-15, VA-66 and VA-251 have been internationally deposited to the NATIONAL INSTITUTE OF BIOSCIENCE AND HUMAN-TECHNOLOGY (NIBH) of Agency of Industrial Science and Technology, 1-3, Higashi 1-chome, Tsukuba-shi, Ibaraki-ken, on Mar. 22, 1994 with the deposit No. FERM BP-4613, on Aug. 4, 1994 with the deposit No. FERM BP-4770, and on Aug. 4, 1994 with the deposit No. FERM BP-4771, respectively.

ATCC 19606 is a microorganism listed on American Type Culture Collection, Catalogue of Bacteria and Phages, 1987 Edition and is easily available.

As a carbon source in a medium to be used for culture of the indigo-producing bacteria, for example, an organic acid such as fumaric acid, citric acid, malic acid and acetic acid; ethanol and benzoic acid may be used. Among them, acetic acid, fumaric acid, ethanol and citric acid may preferably be used.

As a nitrogen source, for example, an ammonium salt such as ammonium chloride, ammonium sulfate and ammonium phosphate; a nitrate such as sodium nitrate, potassium nitrate and ammonium nitrate; and ammonia may be used.

As an inorganic material, for example, potassium phosphate, magnesium sulfate, iron, manganese, zinc or copper may be used. If necessary, a vitamin, an amino acid, and natural nutritional source such as yeast extract and peptone may be added.

The bacteria may be cultured at a cultivation temperature of 20° to 45° C., preferably 30° to 37° C. under aerobic conditions such as aeration-agitation and shaking culture. The cultural medium during the cultivation has a pH of 6 to 9, preferably 7 to 8. The pH of the medium during the culture may be adjusted by adding an acid or an alkali.

The process of the present invention can be carried out by using the medium after the culture as above, bacterial cell collected from the medium by centrifugation or treated products thereof.

The bacterial cell may be used as such after it is collected from the medium, or may be used after washed with a suitable buffer such as a 0.05 to 0.2M phosphate buffer having a pH of 6 to 9.

The above treated products mean crushed products obtained by crushing the bacterial cells collected from culture broth with ultrasonic waves or compression, an extract of the crashed products with water or buffer solution, a purified enzyme obtained from the extract with a treatment such as ammonium sulfate precipitation or column chromatography, and an immobilized product resulting from immobilization of the cells, the crashed product, the extract or the purified enzyme. The cells may be immobilized by using a method of immobilization in a suitable carrier such as polyacrylamide, arginic acid or carrageenan according to a usually used known method.

By bringing the thus obtained indigo-producing bacteria which belongs to genus Acinetobacter or treated products thereof into contact with an aqueous solution which contains at least indole, indigo can be formed and accumulated in the aqueous solution.

As the process for bringing the indigo-producing bacterium which belongs to genus Acinetobacter or treated products thereof into contact with an aqueous solution which contains at least indole, there may be mentioned a fermentation and an enzymatic reaction. The fermentation mentioned here is a method which comprises forming indigo accompanied by growth of a microorganism to be used in an aqueous medium containing all components essential for the growth of the microorganism under conditions of moderate temperature and pH. The enzymatic reaction is a method which comprises cultivating a microorganism to be used by a suitable medium and forming indigo in an aqueous solution which does not necessarily contain essential components for the growth of the microorganism by using the obtained bacterial cells or treated products thereof.

In the fermentation, the above-described medium after culture or the bacterial cell may be used as the indigo-producing bacteria. As the medium, a medium obtained by adding indole to a medium which contains the above-described carbon source, nitrogen source, inorganic salt and the other nutrients as aqueous solutions may be used.

The concentration of indole in the medium is not particularly limited as far as the above indigo-producing bacteria can produce indigo at the concentration, and the indole may preferably be added in block or successively so that the indole concentration does not exceed 0.8 mM.

An amino acid or a salt thereof may be also added to the medium. As the amino acid, for example, there may be mentioned glutamic acid, glutamine and alanine. Among them, L-glutamic acid is most preferred. As the salt, there may be mentioned for example, a sodium salt and a potassium salt. The amino acid or a salt thereof may be used singly or in combination with each other. The amino acid or a salt thereof may be added within the range of 0.5 to 50 mM, preferably 1 to 20 mM and may preferably be added in the middle to later period of the fermentation.

The fermentation may be carried out at a temperature of 20° to 45°, preferably 30° to 37° C., and the medium has a pH of 6 to 9, preferably 7 to 8 during the fermentation. The pH may be adjusted by adding an acid or an alkali. The culture may be usually carried out under aerobic conditions such as aeration-agitation and shaking culture for about 10 to about 72 hours.

By cultivating the bacteria as above, indigo can be formed and accumulated in the medium in a significant amount.

In the enzymatic reaction, as the indigo-producing bacteria or treated products thereof, the above-described bacterial cell or treated products thereof may be used. As the aqueous solution, there may be used an aqueous solution or an appropriate buffer each of which contains at least indole, and, for example, a buffer such as a 0.05 to 0.2M phosphate buffer may be used.

The amount of the bacterial cells or treated products thereof prepared as above is not particularly limited and is generally 0.5 to 10% by weight/volume based on the volume of the aqueous solution.

The concentration of indole in the aqueous solution is not particularly limited as far as the indole is converted with an enzymatic reaction into indigo at the concentration, and may preferably be added in block or successively so that the indole concentration does not exceed 0.8 mM.

An amino acid or a salt thereof may be added to the aqueous solution. As the amino acid, for example, there may be mentioned glutamic acid, glutamine and alanine. Among them, L-glutamic acid is most preferred. As the salt, there may be mentioned, for example, a sodium salt and a potassium salt. The amino acid or a salt thereof may be used singly or in combination with each other. The amino acid or a salt thereof may be added within the range of 0.5 to 20 mM, preferably 1 to 15 mM, and may preferably be added in the starting period of the enzymatic reaction.

The enzymatic reaction may be carried in the aforesaid aqueous solution at a temperature of 20° to 45° C., preferably 30° to 37° C., and at a pH of 6 to 9, preferably 7 to 8. The pH may be adjusted by adding an acid or an alkali. The enzymatic reaction may be usually carried out under aerobic conditions such as aeration-agitation and shaking for about 5 to about 48 hours.

By carrying out the enzymatic reaction as above, indigo can be formed and accumulated in the aqueous solution in a significant amount.

After indigo is formed and accumulated by the above fermentation or enzymatic reaction, indigo can be collected from the aqueous solution according to a usual known method for separation and purification. For example, indigo is extracted with an organic solvent such as ethyl acetate, dimethyl sulfoxide and chloroform and the solvent is evaporated to get an indigo crystal. Also, indigo is dissolved in an aqueous solution to which sodium dithionite has been added under an alkaline condition and the bacterial cells are removed by ultrafiltration, and then, indigo is oxidized with air to get indigo crystals.

According to the present invention, indigo can be efficiently prepared in a higher yield based on the amount of the raw material as compared with usual processes for preparing indigo.

EXAMPLES

The present invention is described in detail by referring to Examples, but the following Examples are described only as an aid for concretely identifying the present invention and the scope of the invention is not limited by these Examples.

Example 1

(a) A medium which comprises 3 g of $(NH_4)_2SO_4$, 0.5 g of $KH_2PO_4$; 0.5 g of $K_2HPO_4$, 0.5 g of $MgSO_4.7H_2O$, 0.5 g of NaCl, 10 mg of $FeSO_4.7H_2O$, 10 mg of $CaCl_2.2H_2O$, 1 g of yeast extracts and 1000 ml of distilled water having a pH of 7.0 was prepared and 100 ml of the medium was apportioned into two 500 ml-Erlenmeyer flasks and sterilized at 120° C. for 15 minutes. Then, 1 ml of ethanol was added to each flask and the medium was inoculated with Acinetobacter species MY-15 strain (FERM BP-4613) and was subjected to shaking culture at 30° C. for 24 hours.

(b) A 5 liter-Erlenmeyer flask was charged with 500 ml of the same medium as above and sterilized at 120° C. for 15 minutes. Then, 5 ml of ethanol and 100 mg of indole were added and the medium was inoculated with 10 ml of the above shaking culture, and the medium was subjected to shaking culture at 30° C. for 24 hours. During the culture, 100 mg of indole was further added after 12 hours from the initiation of the shaking culture. One hundred ml of ethyl acetate was added to the obtained fermentation broth to extract a formed blue pigment. The ethyl acetate fraction was collected by separation and ethyl acetate was evaporated under reduced pressure to have 35 mg of blue crystals. The analytical results of the blue crystals revealed that the blue crystals had the same Rf value on the chromatography, visible spectrum and UV spectrum with those of the standard indigo (Guaranteed Reagent, manufactured by Wako Pure Chemical), respectively.

Example 2

(a) A medium which comprises 3 g of $(NH_4)_2SO_4$, 0.5 g of $KH_2PO_4$; 0.5 g of $K_2HPO_4$, 0.5 g of $MgSO_4.7H_2O$, 0.5 g of NaCl, 10 mg of $FeSO_4.7H_2O$, 10 mg of $CaCl_2.2H_2O$, 1 g of yeast extracts and 1000 ml of distilled water having a pH of 7.0 was prepared and 100 ml of the medium was apportioned into two 500 ml-Erlenmeyer flasks and sterilized at 120° C. for 15 minutes. Then, 1 ml of ethanol was each added to the medium and the medium was inoculated with Acinetobacter species MY-15 strain (FERM BP-4613) and was subjected to shaking culture at 30° C. for 24 hours.

(b) A 5 liter-Erlenmeyer flask was charged with 1,000 ml of the same medium as above and sterilized at 120° C. for 15 minutes. Then, 10 ml of ethanol was added and the medium was inoculated with 20 ml of the above shaking culture, and the medium was subjected to shaking culture at 30° C. for 24 hours. The obtained culture broth was centrifuged at 8,000 rpm at 4° C. for 15 minutes to collect bacterial cells, and the cells were subjected to tests as mentioned below.

(c) The collected cells were washed once with 200 ml of 0.1M phosphate buffer having a pH of 7 and suspended in 500 ml of the same buffer. To the buffer was added 100 mg of indole and the mixture was allowed to react at 30° C. for 24 hours. During the culture, 100 mg of indole was further added after 12 hours from the initiation of the enzymatic reaction. After the completion of the reaction, 100 ml of ethyl acetate was added to the reaction mixture to extract formed blue pigment, and the ethyl acetate fraction was collected. Then, ethyl acetate was evaporated under reduced pressure to have 40 mg of blue crystals. The analytical results of the blue crystals revealed that the blue crystals had the same Rf value on chromatography, visible spectrum and UV spectrum with those of the standard indigo (Guarantee Reagent manufactured by Wako Pure Chemical), respectively.

Example 3

(a) A medium which comprises 3 g of $(NH_4)_2SO_4$, 0.5 g of $KH_2PO_4$; 0.5 g of $K_2HPO_4$, 0.5 g of $MgSO_4.7H_2O$, 0.5 g of NaCl, 10 mg of $FeSO_4.7H_2O$, 10 mg of $CaCl_2.2H_2O$, 10 g of sodium acetate, 1 g of an yeast extract and 1000 ml of distilled water having a pH of 7.0 was prepared and 200 ml of the medium was apportioned into two 500 ml-Erlenmeyer flasks and sterilized at 120° C. for 15 minutes. Then, the medium was inoculated with *Acinetobacter calcoaceticus* ATCC 19606 strain and was subjected to shaking culture at 30° C. for 24 hours.

(b) The bacterial cells were collected and washed once with 50 ml of physiological saline, and the whole cells were suspended in 100 ml of a 0.1M phosphate buffer having a pH of 7.0 which contains 5% of glycerol. The suspension was added 20 mg of indole and the mixture was allowed to react at 30° C. for 48 hours. During the reaction, 20 mg of indole was further added after 24 hours from the initiation of the reaction. After the completion of the reaction, 50 ml of ethyl acetate was added to the reaction mixture to extract formed blue pigment, and the ethyl acetate fraction was collected. Then, ethyl acetate was evaporated under reduced pressure to have 3.5 mg of blue crystal. The analytical results of the blue crystal revealed that the blue crystal had the same Rf value on chromatography, visible spectrum and UV spectrum with those of the standard indigo (Guarantee Reagent, manufactured by Wako Pure Chemical), respectively.

Example 4

(a) Two 500 ml-Erlenmeyer flasks were each charged with 200 ml of the medium prepared in the same manner as in Example 3 (a) and sterilized at 120° C. for 15 minutes. Then, the medium was inoculated with Acinetobacter species VA-66 strain (FERM BP-4770) and was subjected to shaking culture at 30° C. for 24 hours.

(b) The bacterial cells were collected and washed once with 50 ml of physiological saline, and the whole cells were suspended in 100 ml of a 0.1M phosphate buffer having a pH of 7.0 which contains 5% of glycerol. The suspension was added 20 mg of indole and the mixture was allowed to react at 30° C. for 48 hours. During the reaction, 20 mg of indole was further added after 24 hours from the initiation of the reaction. After the completion of the reaction, 50 ml of ethyl acetate was added to the reaction mixture to extract a formed blue pigment, and the ethyl acetate fraction was collected. Then, ethyl acetate was evaporated under reduced pressure to have 4.5 mg of blue crystals. The analytical results of the blue crystals revealed that the blue crystals had the same Rf value on chromatography, visible spectrum and UV spectrum with those of the standard indigo (Guarantee Reagent manufactured by Wako Pure Chemical), respectively.

Example 5

(a) Two 500 ml-Erlenmeyer flasks were each charged with 200 ml of the medium prepared in the same manner as in Example 3 (a) and sterilized at 120° C. for 15 minutes. Then, the medium was inoculated with Acinetobacter species VA-251 strain (FERM BP-4771) and was subjected to shaking culture at 30° C. for 24 hours.

(b) The bacterial cells were collected and washed once with 50 ml of physiological saline, and the whole cells were suspended in 100 ml of a 0.1M phosphate buffer having a pH of 7.0 which contains 5% of glycerol. The suspension was added 20 mg of indole and the mixture was allowed to react at 30° C. for 48 hours. During the reaction, 20 mg of indole was further added after 24 hours from the initiation of the reaction. After the completion of the reaction, 50 ml of ethyl acetate was added to the reaction mixture to extract a formed blue pigment, and the ethyl acetate layer was collected. Then, ethyl acetate was evaporated under reduced pressure to have 4.0 mg of blue crystals. The analytical results of the blue crystals revealed that the blue crystals had the same Rf value on chromatography, visible spectrum and UV spectrum with those of the standard indigo (Guarantee Reagent manufactured by Wako Pure Chemical), respectively.

Example 6

(a) Two 500 ml-Erlenmeyer flasks were each charged with 100 ml of the medium prepared in the same manner as in Example 1 (a) and sterilized at 120° C. for 15 minutes. Then, 1 ml of ethanol was each added to the medium and the medium was inoculated with Acinetobacter species MY-15 strain (FERM BP-4613) and was subjected to shaking culture at 30° C. for 24 hours.

(b) A 5 liter-Erlenmeyer flask was charged with 1000 ml of the same medium as above (a) and sterilized at 120° C. for 15 minutes. Then, 10 ml of ethanol was added to the medium and the medium was inoculated with 20 ml of the above shaking culture, and the medium was subjected to shaking culture at 30° C. for 24 hours. The obtained culture was centrifuged at 8,000 rpm at 4° C. for 15 minutes to collect bacterial cells. The thus obtained cells were subjected to tests as below.

(c) The collected cells were washed once with 200 ml of a 0.1M phosphate buffer having a pH of 7 and suspended in 500 ml of a reaction solution to which L-glutamic acid had previously been added at a concentration as shown in Table 1. Then, 100 mg of indole was added to carry out the reaction at 30° C. for 24 hours. During the reaction, 100 mg of indole was further added after 12 hours from the initiation of the reaction. After the completion of the enzymatic reaction, 200 ml of ethyl acetate was added to the reaction mixture to extract formed indigo and the ethyl acetate fraction was collected to obtain the formed indigo. The results are shown in Table 1.

TABLE 1

| Glutamic acid concentration (mM) | Relative amount of formed indigo |
| --- | --- |
| No addition | 100 |
| 0.2 | 105 |
| 1 | 140 |
| 5 | 160 |
| 10 | 145 |
| 20 | 115 |

From the results shown in Table 1, it was confirmed that a yield of indigo had been increased by adding an amino acid.

Example 7

(a) Acinetobacter species MY-15 strain (FERM BP-4613) was subjected to shaking culture in the same manner as in Example 1 (a).

(b) A 5 liter-Erlenmeyer flask was charged with 500 ml of the same medium as above and sterilized at 120° C. for 15 minutes. Then, 5 ml of ethanol and 100 mg of indole were added to the medium and the medium was inoculated with 10 ml of the above shaking culture, and the medium was subjected to shaking culture at 30° C. for 24 hours. During the culture, 100 mg of indole and sodium L-glutamate at a concentration as shown in Table 1 were added after 12 hours from the initiation of the shaking culture. After termination of the fermentation, 200 ml of ethyl acetate was added to the thus obtained fermentation liquid to extract formed indigo and the ethyl acetate fraction was collected to obtain the formed indigo. The results are shown in Table 2.

TABLE 2

| Sodium glutamate concentration (mM) | Relative amount of formed indigo |
| --- | --- |
| No addition | 100 |
| 0.2 | 105 |
| 1 | 120 |
| 5 | 135 |
| 20 | 140 |
| 50 | 120 |

From the results shown in Table 2, it was confirmed that a yield of indigo had been increased by adding an amino acid.

We claim:

1. A process for preparing indigo which comprises bringing an indigo-producing bacteria belonging to genus Acinetobacter which is at least one selected from the group consisting of Acinetobacter species MY-15, *Acinetobacter calcoaceticus* ATCC 19606, Acinetobacter species VA-66 and Acinetobacter species VA-251 into contact with an aqueous solution containing at least indole to have indigo formed and accumulated in the aqueous solution; and collecting indigo from the aqueous solution.

2. The process for preparing indigo according to claim 1, wherein indole is contained in an amount of 0.8 mM or less in the aqueous solution.

3. The process for preparing indigo according to claim 1, wherein the indigo-producing bacteria belonging to genus Acinetobacter is brought into contact with the aqueous solution containing indole by fermentation.

4. The process for preparing indigo according to claim 1, wherein the indigo-producing bacteria belonging to genus Acinetobacter is brought into contact with the aqueous solution containing indole by an enzymatic reaction.

5. The process for preparing indigo according to claim 3, wherein the aqueous solution further contains an amino acid or a salt thereof.

6. The process for preparing indigo according to claim 5, wherein the amino acid is at least one selected from the group consisting of glutamic acid, glutamine and alanine.

7. The process for preparing indigo according to claim 6, wherein the amino acid is L-glutamic acid or a salt thereof.

8. The process for preparing indigo according to claim 7, wherein the amino acid or a salt thereof is contained in an amount of 0.5 to 50 mM in the aqueous solution.

9. The process for preparing indigo according to claim 8, wherein the amino acid or a salt thereof is contained in an amount of 1 to 20 mM in the aqueous solution.

10. The process for preparing indigo according to claim 4, wherein the aqueous solution further contains an amino acid or a salt thereof.

11. The process for preparing indigo according to claim 10, wherein the amino acid is at least one selected from the group consisting of glutamic acid, glutamine and alanine.

12. The process for preparing indigo according to claim 11, wherein the amino acid is L-glutamic acid or a salt thereof.

13. The process for preparing indigo according to claim 12, wherein the amino acid or a salt thereof is contained in an amount of 0.5 to 20 mM in the aqueous solution.

14. The process for preparing indigo according to claim 13, wherein the amino acid or a salt thereof is contained in an amount of 1 to 15 mM in the aqueous solution.

* * * * *